United States Patent
Kodgule et al.

(10) Patent No.: US 8,540,678 B2
(45) Date of Patent: Sep. 24, 2013

(54) DEVICE AND A SYSTEM FOR DELIVERY OF BIOLOGICAL MATERIAL

(75) Inventors: Mandar Kodgule, Mumbai (IN); Sachidananda Yallambalsi, Aurangabad (IN)

(73) Assignee: Wockhardt Ltd., Bandra-Kurla Complex, Bandra East, Mumbai (IN)

( * ) Notice: Subject to any disclaimer, the term of this patent is extended or adjusted under 35 U.S.C. 154(b) by 272 days.

(21) Appl. No.: 12/996,368

(22) PCT Filed: Jun. 5, 2009

(86) PCT No.: PCT/IB2009/052382
§ 371 (c)(1),
(2), (4) Date: Feb. 28, 2011

(87) PCT Pub. No.: WO2009/147641
PCT Pub. Date: Dec. 10, 2009

(65) Prior Publication Data
US 2011/0196308 A1      Aug. 11, 2011

(30) Foreign Application Priority Data

Jun. 6, 2008   (IN) .................. 1212/MUM/2008
Jun. 6, 2008   (IN) .................. 1213/MUM/2008
Jun. 6, 2008   (IN) .................. 1214/MUM/2008

(51) Int. Cl.
*A61M 5/00*         (2006.01)

(52) U.S. Cl.
USPC .......................... 604/173; 604/22; 606/186

(58) Field of Classification Search
USPC ....................... 604/173, 22, 272; 606/186
See application file for complete search history.

(56) References Cited

U.S. PATENT DOCUMENTS

| | | |
|---|---|---|
| 5,527,288 A | 6/1996 | Gross et al. |
| 5,860,957 A | 1/1999 | Jacobsen et al. |
| 2007/0073267 A1 | 3/2007 | Muller et al. |
| 2007/0088271 A1 | 4/2007 | Richards |
| 2008/0275400 A1* | 11/2008 | Ferguson ............. 604/173 |

FOREIGN PATENT DOCUMENTS

| | | |
|---|---|---|
| WO | WO03026726 A1 | 4/2003 |
| WO | WO2006060106 A1 | 6/2006 |
| WO | WO2006127905 A2 | 11/2006 |
| WO | WO2007108987 A2 | 9/2007 |

* cited by examiner

*Primary Examiner* — Kevin C Sirmons
*Assistant Examiner* — Deanna K Hall
(74) *Attorney, Agent, or Firm* — Bio Intellectual Property Services LLC (Bio IPS); O. (Sam) Zaghmout

(57) ABSTRACT

The present application provides a device and a system for the delivery of biological material across the biological tissue. The device may be for the programmed delivery of biological material through a needle or a micro-needle or micro-needles or biodegradable microneedles.

12 Claims, 6 Drawing Sheets

MECHANISM FOR DOSE SETTING AND SYSTEM FOR
DISCHARGE OF BIODEGRADABLE MICRO-NEEDLE

FIGURE 1 MECHANISM FOR PROGRAMMED DELIVERY OF BIOLOGICAL MATERIAL
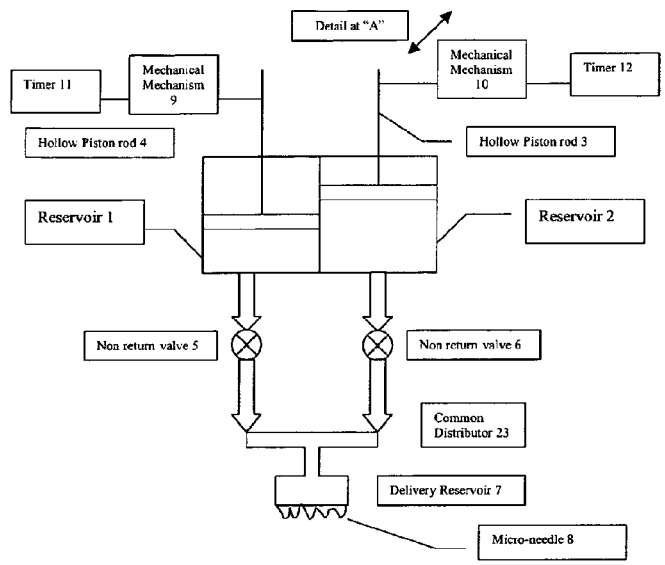
Details at A
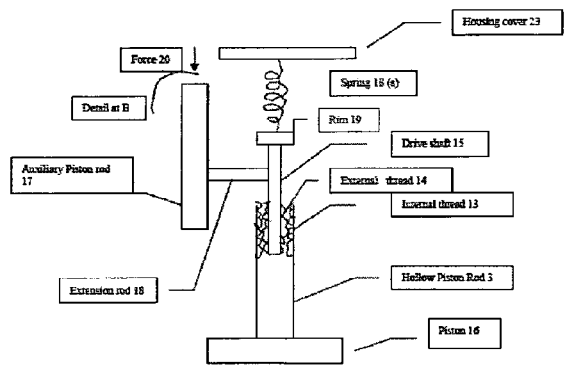
Details at B
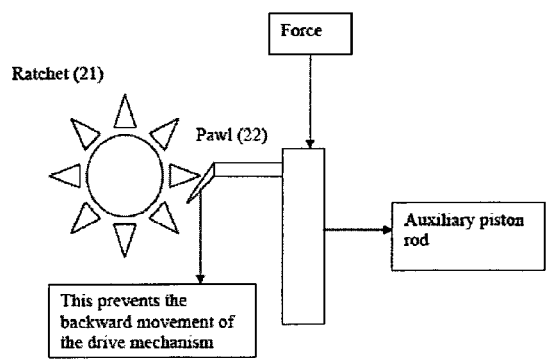

FIGURE 2 MECHANISMS FOR PROGRAMMED DELIVERY OF BIOLOGICAL MATERIAL

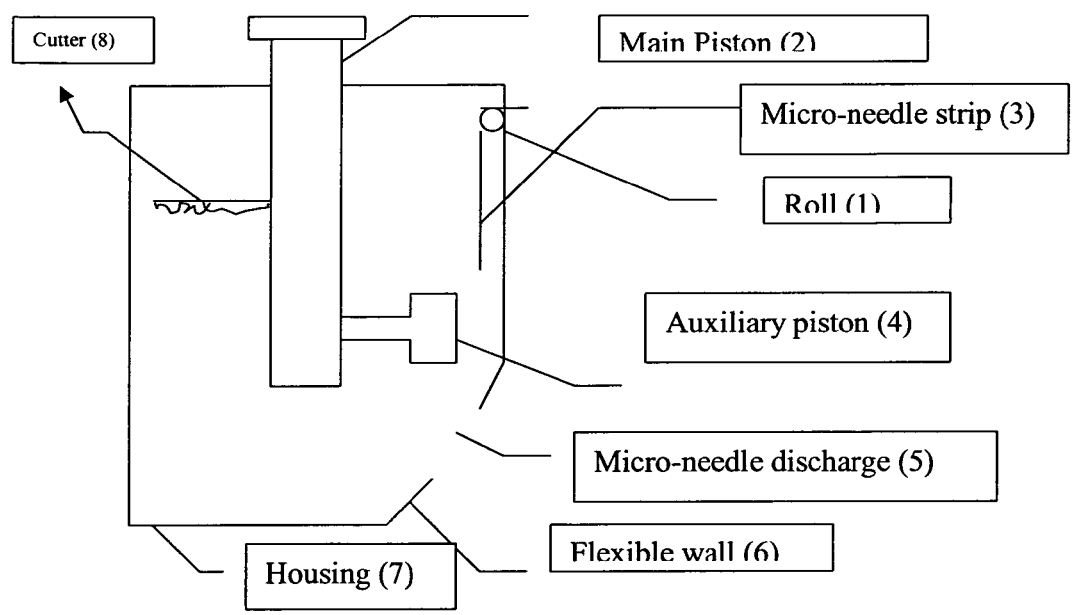
FIGURE 3 : MECHANISM FOR DOSE SETTING AND SYSTEM FOR DISCHARGE OF BIODEGRADABLE MICRO-NEEDLE

FIGURE 4: MECHANISM FOR CUTTING STRIP OF BIODEGRADABLE MICRO-NEEDLE
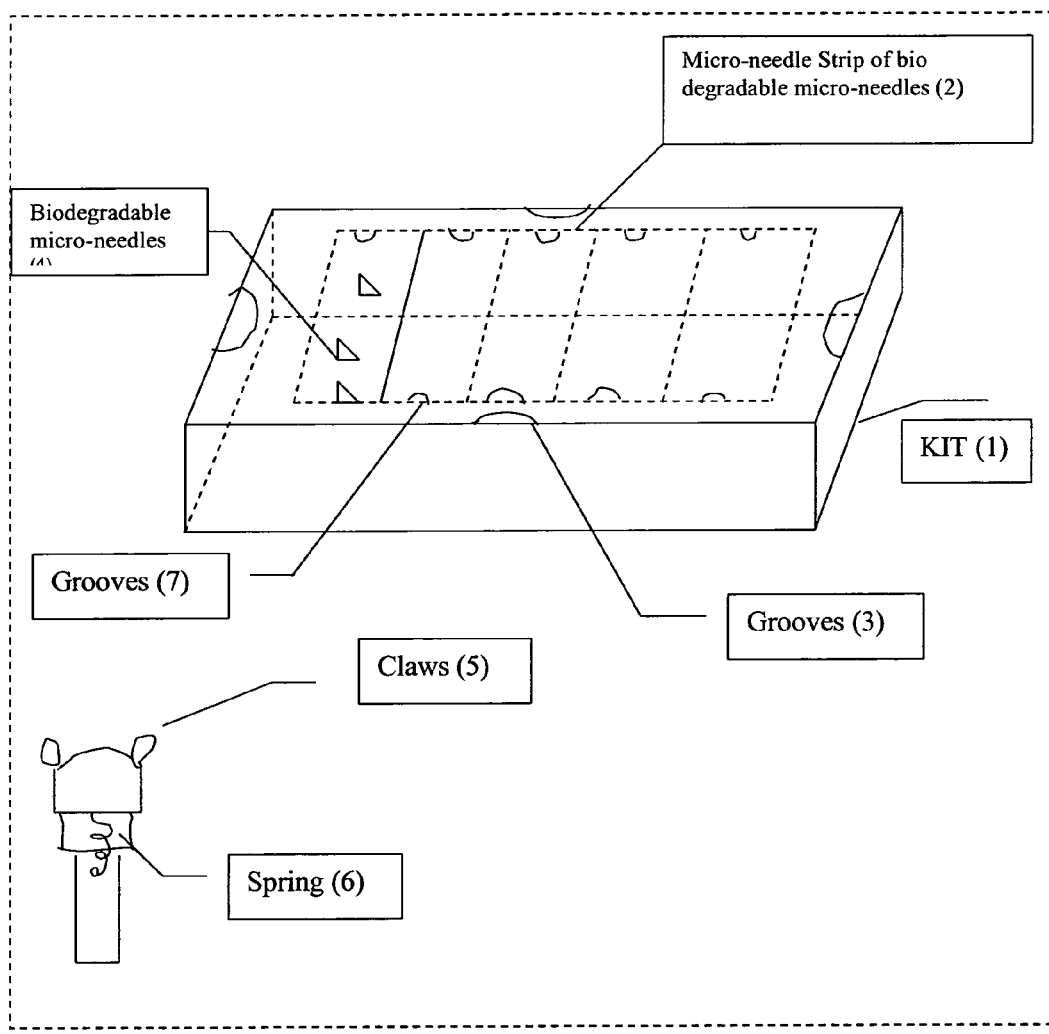

FIGURE 5: MECHANISM FOR DISCHARGE OF BIOLOGICAL MATERIAL THROUGH NEEDLE ATTACHED TO A PEN DEVICE

FIGURE 6: MECHANISMS FOR DISCHARGE OF BIOLOGICAL MATERIAL THROUGH MICRO-NEEDLE ATTACHED TO A PEN DEVICE

- Pen Device 1
- Syringe 2
- Rubber 3
- Metal seal 4

Existing syringe and pen

- Needle cap 5
- Micro-Needle
- Internal thread 6

Needle and cap

DEVICE AND A SYSTEM FOR DELIVERY OF BIOLOGICAL MATERIAL

FIELD OF THE INVENTION

The present invention provides a device and a system for the delivery of biological material across the biological tissue. The device may be for the programmed delivery of biological material through a needle or a micro-needle or micro-needles or biodegradable micro-needles. One of the embodiments of the device may be for the programmed delivery of biological material across the biological tissue which comprises two reservoirs one of which delivers the biological material immediately and the other reservoir delivers the biological material over a specified time. Separate drive mechanisms deliver the biological material in a programmed fashion. Another embodiment of the device may be for the delivery of biodegradable micro-needle across a biological barrier, wherein the device comprises a micro-needle strip comprising of biodegradable micro-needles and a mechanism to cut the selected portion of biodegradable micro-needle corresponding to the selected dose of the microneedles. It may also relate to a method of delivering the biodegradable micro-needle. Yet another embodiment of device may be for the delivery of biological material across the biological tissue with minimal or no pain, damage and irritation to the tissue. The device comprises one micro-needle attached to a needle cap wherein the needle cap is attached to an injection pen device.

BACKGROUND OF THE INVENTION

Dosed biological material delivery devices, often referred to as 'injection pen device' are commonly used for routine injection of biologic materials. Hence, 'injection pen device' refer generally to any and all free-standing portable device containing a plurality of doses of a biological material liquid which can be operated by a patient for self injection to deliver metered doses of the liquid to the patient's body on a plurality of occasions.

Injection pen device are normally used to deliver the basal doses of biological material. Further prior art devices for basal and bolus delivery of biological materials are available wherein (i) They deliver precisely either the basal doses of biological material or bolus doses of biological material but not both by the drive mechanism simultaneously. Predominantly the drive mechanisms used are either (i) a gas source or (ii) a combination of gas source and a mechanically stored energy or (iii) a purely mechanically stored energy. In situations where purely mechanical energy is being used, either a basal delivery of biological material or bolus delivery of biological material is achieved, but not both of them.

(ii) The devices which employ only mechanical energy as a sole mechanism of delivery, it delivers only bolus or basal delivery of biological material but not both.

(iii) The devices which employ transfer of mechanical energy to hydraulic energy and back to mechanical energy achieves both bolus delivery of biological material and basal delivery of biological material.

The term 'micro-needle' may refer to a device for transdermal delivery or removal of fluids without many of the risks associated with standard syringes. Such devices may use arrays of small diameter micro-needles and these small diameter micro-needles may be non-biodegradable or biodegradable. The term 'biodegradable micro-needle' refers to micro-needles made of biodegradable polymers which include polymers of hydroxy acids such as lactic acid and glycolic acid polylactide, polyglycolide, polylactide-co-glycolide, and copolymers with PEG, poly anhydrides, poly (ortho) esters, polyurethanes, poly(butyric acid), poly (valeric acid), and poly (lactide-co-caprolactone) comprising a biological material which possesses therapeutic, prophylactic, or diagnostic properties in vivo, for example when administered to an animal, including mammals, such as humans.

Biological material delivered by these biodegradable micro-needles may provide a clinically useful alternative to standard syringes. The devices comprising biodegradable micro-needles may be known in the art for delivering a wide variety of biological materials. The amount of selected portion of biodegradable micro-needle corresponding to the dose to be delivered may vary from individual to individual. Adjusting the selected portion of biodegradable needle corresponding to the dose according to individual need is a challenging task with biodegradable micro-needles as the biological material that needs to be delivered may be fixed per micro-needle and there may be no reservoir attached for increasing the dose.

Micro-needle which is non biodegradable is designed to pierce the stratum corneum skin barrier layer in a minimally invasive and pain-free manner to provide transient pathways for the delivery of macromolecules to the underlying skin epidermis. Since the needle is short, it does not reach the nerve-rich regions of the lower parts of the skin. As a consequence, the stimulus caused by micro-needle insertion into the skin is weak and cause less pain. Such devices may use arrays of small diameter needles that each deliver relatively small flow rates of fluid across or into a biological barrier, which together with the fluid delivered by other needles in the array; provide a clinically useful alternative to standard syringes.

U.S. Pat. No. 6,702,779 discloses a wearable, self-contained drug infusion device that is capable of achieving the precise flow rate control needed for dose-critical drugs such as insulin.

U.S. Pat. No. 6,939,324 discloses fluid delivery and measurement systems and methods.

US Application No 20050119618 discloses a hydraulic pump device and its use thereof, especially in a fluid delivery system.

PCT Application No WO07115039 relates generally to fluid delivery devices and particularly to fluid delivery devices capable of delivering one or more medicaments to a patient to provide a sustained, basal delivery and/or a bolus delivery of each medicament.

U.S. Pat. Nos. 7,056,495, 6,586,006, 6,565,871, 6,331, 310, 6,290,991, 6,811,792 and 6,893,657 disclose solid dose delivery systems for administration of guest substances and bioactive material to subcutaneous and intradermal tissue, the delivery vehicle being sized and shaped for penetrating the epidermis.

U.S. Pat. No. 7,141,034 relates to transdermal drug delivery device for forming a micropore in a tissue membrane of an animal comprising a substrate and a porator that is located on or within the substrate.

U.S. Pat. No. 7,083,592 relates to apparatus for delivering or withdrawing fluid, e.g. a drug, through the skin.

US Application No. 20050008683 relates to a method for administration of a substance to a subject's skin comprising delivering the substance into an intra dermal compartment of the subject's skin, wherein the substance results in an immune response no greater than when the substance is delivered intramuscularly.

US Application No. 20050010193 relates to a method for administration of a substance into a subject's skin, comprising delivering the substance into a junctional layer of the subject's skin.

EP Patent No. 1 880 741 A1 discloses a method for directly delivering whereby a substance is introduced into an intradermal space within mammalian skin which involves administering the substance through at least one small gauge hollow needle having an outlet with an exposed height between 0 and 1 mm.

SUMMARY OF THE INVENTION

The present inventors while working for suitable devices for programmed delivery of biological materials have found that there is a need
  (i) Programmed delivery of biological materials
  (ii) A device and a system for delivery of biodegradable micro-needles
  (iii) Delivery of biological material through a single needle which acts as a micro-needle For the programmed delivery of biological materials there is a need
  (i) For a mechanism which make use of only one source of energy i.e. mechanical energy and minimum number of components and yet perform the task.
  (ii) For more than one reservoir wherein same or different biological materials are stored in separate reservoirs.

The term 'Programmed Delivery' of biological material as used herein refers to delivery of biological material in a dual phase manner. Further the 'Dual Phase' as used herein refers to such a delivery wherein one phase delivers biological material immediately and the other phase delivers the biological material in a specified time.

Dual phase delivery may be used interchangeably for bolus and basal delivery of biological material.

'Programmed delivery' may be tailored to delivery of immediate delivery (bolus) of biological material followed by delivery of biological material over a specified time (basal) further followed by delivery of immediate delivery (bolus) of biological material and the like as and when need arises.

One of the aspects of present invention provides for a fluid delivery device for programmed delivery of biological materials across biological barrier wherein the device comprises (a) At least two reservoirs (b) A drive mechanism (c) A means for actuating drive mechanism (d) At least one needle or micro-needle As used herein, the term ' biological material' refers to an agent which possesses therapeutic, prophylactic, or diagnostic properties in vivo, for example when administered to an animal, including mammals, such as humans. The biological material is selected from the group comprising of peptides, proteins, carbohydrates, nucleic acid molecules, lipids and other pharmaceutically active ingredients or combinations thereof.

The pharmaceutically active ingredients may be one or more of anesthetics, analgesics, anti bacterials, anti virals, antiadrenergics, antiamebics, antianginals, antiarrhythmics, antibiotics, anticoagulants, anticonvulsants, antidepressants, antidiabetics, antidiuretics, antidyskinetics, antiemetics, antifungals, antihistaminics, antihyperparathyroids, antihypertensives, antiinflammatories, antimigraines, antineoplastics, antineoplastics, antiprotozoals, antipsychotics, antispasmodics, antithrombotics, antiulceratives, anxiolytics, astringents, bone resorption inhibitors, bronchodilators, cardiotonics, cholinergics, diaprostic agents, diuretics, hormones, steriods, hydrochloride as anineoplastic, hypnotics, immunomodulators, immunosuppresants, mucolytics, muscle relaxants, neuromuscular blocking agents, oxytocics, vasodilator and the like.

The pharmaceutically active ingredients may further include one or more ketamine, chloroprocaine hydrochloride, alfentanil, amikacin, abacavir, bretylium tosylate, metronidazole, diltiazem hydrochloride, ciprofloxacin, dextran sulfate sodium, fosphenytoin sodium, rubidium chloride, insulin, desmopressin acetate, haloperidol lactate, dimenhydrinate, abelcet, diphenhydramine hydrochloride, paricalcitol, diltiazem hydrochloride, ketorolac, dihydroergotamine mesylate, mitoxantrone hydrochloride, leuprolide acetate, metronidazole, aripiprazole, dicyclomine hydrochloride, dipyridamole, cimetidine hydrochloride, diazepam, zinc chloride, zoledronic acid, aminophyllin, digoxin, pyridostigmine bromide, diatrizoate sodium, furosemide, estrogen, androgen and the like, steriods such as glucocorticoid and the like, mechlorethamine hydrochloride, etomidate, mitoxantrone hydrochloride, tacrolimus, acetylcysteine, baclofen, vecuronium bromide, oxytocin nitroglyceine and the like.

The geometrical shape of micro-needles may be selected from the group comprising of cylindrical, pyramidal, frustoconical and frustopyramidal.

The micro-needles either made of metal or biodegradable polymers may be formed with shafts that have a circular cross-section in the perpendicular, or the cross-section may be non-circular. For example, the cross-section of the microneedle can be polygonal (e.g. star-shaped, square, triangular, pyramidal), oblong, or another shape such as frusto conical and frusto pyramidal. The shaft may have one or more bores.

The cross-sectional dimensions of micro-needles or biodegradable micro-needles typically may be between about 1 μm and 500 μm, and preferably between 10 and 100 μm. The outer diameter may be typically between about 10 μm and about 100 μm, and the inner diameter may be typically between about 3 μm and about 80 μm.

The length of the micro-needles or biodegradable microneedles typically may be between about 10 μm and 1 mm, preferably between 100 μm and 500 μm, and more preferably between 150 μm and 350 μm. The length may be selected for the particular application, accounting for both an inserted and un inserted portion. An array of microneedles can include a mixture of micro-needles having, for example, various lengths, outer diameters, inner diameters, cross-sectional shapes, and spacing between the micro-needles. In transdermal applications, the 'insertion depth' of the micro-needles may preferably be less than about 500 μm, so that insertion of the micro-needles into the skin may not penetrate into the dermis, thereby avoiding contacting nerves which may cause pain. In such applications, the actual length of the microneedles typically may be longer, since the portion of the micro-needles distal the tip may not be inserted into the skin; the uninserted length depends on the particular device design and configuration. The actual (overall) height or length of micro-needles should be equal to the insertion depth plus the uninserted length.

Suitable materials for manufacturing micro-needles and reservoirs include one or more metals, ceramics, semiconductors or polymers which may be biodegradable or non biodegradable. The metals may be selected from the group comprising of pharmaceutical grade stainless steel, gold, titanium, nickel, iron, tin, chromium, copper, palladium, platinum, alloys, silicon, silicon dioxide, and combinations thereof.

Standard size needles may be of any size ranging from 22 gauge to 36 gauge or more.

Suitable non-biodegradable polymers may include one or more cellulose, polycarbonate, polyester, or polyacrylamides. The device comprises two reservoirs, wherein one reservoir may deliver biological material immediately and the other reservoir may deliver biological material over a specified time. Biological material to be delivered through the two reservoirs may be same or different. The reservoirs and the delivery reservoir may be made of either metal or non biodegradable polymeric material. The device may be one drive mechanism corresponding to each reservoir and each drive mechanism comprises a piston, hollow piston rod, drive shaft, a spring and a ratchet and pawl. Piston, hollow piston rod, drive shaft, and a ratchet and pawl mechanisms may be made of either metal or non biodegradable polymer. The drive shaft may be located in hollow piston rod and there may be an integral movement of auxiliary piston and piston wherein the auxiliary piston rod may be attached to drive shaft. The ratchet and pawl may facilitate prevention of piston moving back from its new position to earlier position on delivery of the biologic material. There may be a separate known actuating mechanism for each of the drive mechanisms. The actuating mechanism comprises a timer based on which the actuating mechanism triggered. The needle may be of any available conventional standard size or the micro-needles. A method of administering a biologically active material in a programmed manner from a fluid delivery device wherein one or both the reservoirs may deliver the biological material by means of actuating means employing mechanical energy.

The device for programmed delivery of biological material and method of delivery are as described in the description and shown in FIG. 1 & FIG. 2.

While developing a system for delivering the desired dose of a pharmaceutically active ingredient coated or embedded in biodegradable micro-needle, it was observed that if a mechanism for cutting a selected portion of the biodegradable micro-needle corresponding to the dose was used along with a micro-needle strip containing biodegradable micro-needle, it was able to provide a selected dose of biodegradable micro-needle according to individual's need. The device may be simple in design and may involve simple mechanism for the delivery of the selected portion of the biodegradable micro-needle corresponding to the desired dose of the biodegradable micro-needle. The device has user friendly features.

In one of the aspects of the invention is a device for delivery of a biodegradable micro-needle comprising of a therapeutically active principle and a biodegradable polymer across a biological barrier, wherein the device comprises (a) A micro-needle strip comprising of biodegradable micro-needle, and (b) A mechanism to cut selected portion of biodegradable micro-needle corresponding to the selected dose of the biodegradable micro-needle to be delivered; The mechanism further comprises a main piston and an auxiliary piston for positioning and applying the biodegradable microneedles to the skin surface; a roll for loading the micro-needle strip of biodegradable micro-needles; a cutter for cutting the biodegradable micro-needles; a flexible wall comprising an opening for discharge of micro-needles and housing holding all the components of the device; wherein, the micro-needle strips comprising at least one biodegradable micro-needle.

In embodiments where the micro-needles may be formed of biodegradable polymers, however, the mechanical requirement may be less stringent, since the micro-needles or tips thereof may break off, for example in the skin, and may biodegrade. Nonetheless, even a micro-needle comprising a biodegradable micro-needle still may need to remain intact at least long enough for the micro-needle to serve its intended purpose (e.g., its conduit function). Therefore, micro-needles comprising biodegradable micro-needle may provide an increased level of safety, as compared to non-biodegradable ones. The geometrical shape of biodegradable micro-needles can be selected from the group comprising of cylindrical, conical, tapered, pyramidal, frustoconical and frustopyramidal. The cutting mechanism may be a cutter, a razor, a known claw mechanism made of a sharp edged metal. The main piston, auxiliary piston, and the roll may be made of metal, plastic, polymeric material and combination thereof. The biodegradable micro-needles have an outer diameter of from about 10 microns to 100 microns and length of at least 100 microns. The flexible wall may be made of flexible polymeric material.

A method for delivering the biodegradable micro-needle wherein the method comprises (a) Setting up the portion of the biodegradable micro-needle corresponding to the dose of the biodegradable micro-needle to be delivered, (b) Rotating the main piston by half or one rotation in one direction to cut the select portion of the biodegradable micro-needle corresponding to set dose of biodegradable micro-needle, (c) Rotating the main piston by half or one rotation for the next operation in the same direction to position the auxiliary piston for the next operation, (d) applying force on the main piston to position the biodegradable micro-needle on the flexible wall and to deliver the portion of the biodegradable micro-needle corresponding to the set dose of biodegradable micro-needle on to the skin surface, and (e) A release mechanism to reposition the main piston to its original position. The dose setting may involve vertical movement of the micro-needle strip comprising of biodegradable micro-needles by a known mechanism. The application of force on the main piston either for positioning the biodegradable micro-needle or delivery on to the skin surface may use energy stored in a spring or any other known mechanism. The release mechanism may be a known mechanism.

'Biodegradable micro-needle' used in the present invention include bio degradable polymer and one or more of the diagnostic substance, prophylactic substance, therapeutic substance and the like comprising the pharmaceutically active ingredients. The device for delivery of biodegradable micro-needle and method of delivery are as described in the description and shown in FIG. 3 & FIG. 4.

The present inventors while working for suitable micro needle device design have found that it could be possible to effect modification of conventional hypodermic needle to function as a micro-needle device. The present invention provides a device wherein the length of the conventional hypodermic needle attached to a cap may be reduced to function as a micro-needle.

The conventional hypodermic needle attached to a cap may have varying lengths. The projected needle length of the hypodermic needle from the cap outlet may be anywhere between 6 mm to 9 mm. The 30 gauge or 31 gauge conventional needles have outer diameters of 305 µm and 254 µm and inner diameter of around 200 µm.

The various studies on pain perception reveal the following facts.

Up to 150 µm length (pain is almost insignificant)

From 150 µm to 200 µm (weak to very mild perception)

From 500 µm-750 µm and a width of 50 µm (5-10% of the sensation produced by a 26 gage hypodermic needle) i.e. upper end for pain perception commencement can be considered as 500 µm.

This device manufacture requires modification to be effected in the manufacturing process so as to produce needle whose projected out lengths could be less than 1000 µm or of desired length.

One of the aspects of present invention provides device for transport of biological materials across biological barrier wherein the device comprises one hollow needle attached to a needle cap to function as micro-needle.

As used herein, the term 'hollow' means having one annular bore or channel through the interior of the micro-needle, a diameter sufficiently large to permit passage of fluid and/or solid materials through the micro-needle.

'Biological Material Storage' may mean a syringe or cartridge containing suitable pharmaceutical substance.

A pen device that would be used for the administration of set dose of the biological material is detailed below. The pen device may be used for dose titration if a predetermined dose adjustment may be attached. The pen used for precise administration of dose is described in detail with references to the drawing.

The single needle device as a micro-needle is as described in the description and shown in FIG. 5 & FIG. 6.

The details of one or more embodiments of the inventions are set forth in the description below. Other features, objects and advantages of the invention will be apparent from the description and claims.

DETAILED DESCRIPTION OF THE DRAWINGS

FIG. 1 Mechanism for programmed delivery of biological material

FIG. 2 Mechanisms for programmed delivery of biological material

Detail at 'A'

Detail at 'B'

FIG. 3 Shows mechanisms for dose setting and system for discharge of biodegradable micro-needle FIG. 4 Shows mechanisms for cutting strip of biodegradable micro-needle FIG. 5 Shows mechanism for discharge of biological material through needle attached to a pen device—Existing attachment of needle and needle cap FIG. 6 Shows mechanism for discharge of biological material through micro needle attached to a pen device—Proposed micro-needle attachment to needle cap

DETAILED DESCRIPTION OF THE INVENTION

Mechanism for programmed delivery of biological material is as shown in FIG. 1. The device comprises two reservoirs namely reservoir 1 & reservoir 2. In the FIG. 1, the biological material in reservoir 1 may cater to immediate delivery and the biological material in reservoir 2 may cater to over a specified time. However, the biological material in reservoirs 1 and reservoir 2 may be the same or different. Adequate strength reservoir material may be chosen to withstand the tension of the spring during delivery period of the biological material which may extend from 24 hours to 48 hours or more as the case may be.

Reservoir 1 & reservoir 2 may each be provided with a hollow piston rod (3) and piston (16). The biological material delivery may be triggered by a mechanical mechanism (9 or 10). The two mechanical mechanisms may each correspond to delivery of corresponding biological material from each of the reservoirs.

The detail of mechanical mechanism is shown at 'A'.

The mechanical mechanism (9) may comprise a hollow piston rod (3) which has internal thread (13) at its proximal end. A piston is attached at its distal end (16). A solid drive shaft (15) with external thread (14) at its distal end may be located inside the hollow piston rod (3) and the external thread mates with the internal thread (13) of the hollow piston rod. One end of the extension rod (18) may be connected to drive shaft (15) and the other end is connected to auxiliary piston rod (17). A spring (**18*a*) whose one end may be biased against the rim (19) of the drive shaft (15) and the other end may be biased against the housing cover (23**).

Spring (**18*a*) strength may appropriately be determined depending on whether the biological material may be of immediate delivery or over a specified time. It may be normal that spring (18*a*) may be of lower strength for biological material of immediate delivery than that for over a specified time, both biological materials being the same, considering the fact that higher quantity of immediate delivery of biological material may be delivered. The spring (18*a*) strength determined to overcome the resistances of non return valves (5, 6), frictional losses of common distributor and pressure loss associated with delivery reservoir (7). The rate of a spring is the change in the force it exerts, divided by the change in deflection of the spring. For an extension or compression spring it has the units of lbf/in, N/mm, or similar. Spring properties chosen may be such that it would expand equivalent to incremental delivery of constant throughput of either over a specified time or immediate delivery. Known actuating mechanism chosen may be such that application of force (20**) would result in piston movement corresponding to constant delivery of biological material over a specified time.

The mechanical mechanism (10) for the reservoir (2) may be the same as mentioned for the mechanical mechanism (9).

Auxiliary piston rod (17), extension rod (18) and drive shaft (15) may be molded as one unit or attached separately by other means. Hollow piston rod (3) and piston (16) may be attached by threading means.

The mechanical mechanism shown at detail 'A' may be prevented from moving upwards by a ratchet (21) and pawl (22) mechanism whose details are shown at 'B'. The reservoirs (1, 2), mechanical mechanism (9, 10), timers (11, 12), Non return valves (5, 6), delivery reservoir (7) and micro-needle (8) may be housed in a housing (not shown).

Reservoir 1 and reservoir 2 may either have the same cross section piston or different cross section pistons depending on the variation biological material delivery of immediate nature or over a specified time. Larger the cross section of the piston higher may be the delivery of biological material. Non return valves (5, 6) may be provided at the exit of the reservoir (1) and reservoir (2) as a safety measure to prevent the back entry of the biological material intended for the patient. The delivery of the biological material may be through micro-needles (8) or conventional needle.

Timer (11) provided may be set to raise an alarm at a predetermined interval say 1 hour or 2 hour as per convenience. Timer may be mechanical, electromechanical or digital. When the alarm is raised the biological material may be due for administration. Then the force (20) may be applied on the actuating means shown at detail 'A'. The entire assembly of piston (16), hollow piston rod (3), drive shaft (15), and auxiliary piston rod (17) may be held against spring bias and may be moved down by a predetermined distance delivering the biological material through non return valve (5). Actuating mechanism for both the reservoirs may be different. Actuating mechanism may be one in one reservoir and another in another embodiment.

Another embodiment for programmed delivery of biological material is as shown in FIG. 2. In this embodiment, there may be no delivery reservoir like in FIG. 1. Programmed delivery of biological material may be achieved through an angled discharge pipe connected each of the reservoirs (1, 2)

through a common distributor (7). All other features, working mechanisms, components as mentioned with respect to FIG. 1 are the same.

In FIG. 3, a micro-needle strip comprising of biodegradable micro-needles may be (3) wound round a roll (1). The roll may be made of either a metal or non-biodegradable polymer. The roll and micro-needle strip comprising of biodegradable micro-needle may be located inside the housing (7). Housing may also be made of either a metal or non biodegradable polymer. A known mechanism is used to select the number of biodegradable micro-needle strips corresponding to the set dosage of the biodegradable micro-needles. When the dose is selected by the known mechanism, there would be a corresponding vertical down ward movement of the biodegradable micro-needle over the roll.

In one of the embodiments the position of the main piston (2) would be in a reference position to start with. This reference position would correspond to the reference position of the biodegradable micro-needle in its unused condition. The main piston (2) may be made of either metal or non biodegradable polymer.

A cutter (8) may be attached to the main piston (2) either integrally or by other means. The cutter (8) may be positioned circumferentially on the main piston (2) in any of its vertical length. The position of cutter (8) attachment to main piston (2) corresponds to reference position. The cutter may be made of suitable sharp edged metal.

The main piston (2) may be both rotatable and moveable in the longitudinal direction. The main piston (2) may travel only in one longitudinal direction and restrained to move in the opposite direction. The main piston (2) may travel only in the downward direction in the embodiment shown in FIG. 3. A known mechanical mechanism or other means may be used to fulfill the movement in the longitudinal direction and rotation.

An auxiliary piston (4) may be attached to main piston (2) at its distal end. The auxiliary piston (4) may be made either of metal or non-biodegradable polymers. It may be attached either integrally or by other means. Further auxiliary piston (4) attachment position may be at an angle to main piston (2) attachment circumferentially. This angle can vary from 30° to 180°. In the FIG. 3, it is shown to be positioned at 180°. Attachment of auxiliary piston (4) at an angle is to ensure prevention of delivery of the biodegradable micro-needle by accidental application of force and may also prevent the hindrance of auxiliary piston (4) from free fall when the biodegradable micro-needles may be cut.

Both main piston (2) and auxiliary piston (4) may be of any shape such as circular, rectangular, square etc. The FIG. 3 shows the auxiliary piston of circular shape.

Once the dose of biodegradable micro-needle may be set, the main piston (2) may be rotated by either 180° or 360°. When it may be rotated by the predetermined rotation, the set dose of biodegradable micro-needle may be cut and fall on to the sloping flexible wall. After this operation, the auxiliary piston (4) which may be located opposite the main piston (2), may need to be repositioned before the next operation. A further equal rotation 180° or 360° may be performed so as to position the auxiliary piston (4) for the next operation.

Now a suitable force may be applied on the main piston (2) either manually or by other mechanical or electrical means or a combination of both. This force application may be necessary to make ready the position of the biodegradable micro-needle for discharge as shown in FIG. 3. Further application of force discharges the biodegradable micro-needle on to the skin.

Once the biodegradable micro-needle may be discharged, a known release mechanism reverts back the main piston (2) to its original position for the next dose setting and operation.

In FIG. 4, yet another mechanism for cutting a micro-needle strip comprising of biodegradable needle is shown. A micro-needle strip comprising of biodegradable micro-needles (2) may be placed over grooves (3) of a kit (1). Biodegradable microneedles may be projecting inside the kit (1). There are perforations between a select numbers of bio degradable micro-needles. A tool for pick up of select number of bio degradable micro-needles having claws (5) fits into the grooves (7). A spring (6) may provide necessary force to dislodge the select strip of bio degradable needles along the perforations. Since the substrate containing the perforated micro-needles may be rested and supported on grooves (3), removal of a micro-needle strip comprising of bio degradable micro-needle keeps the remaining biodegradable micro-needles intact.

FIG. 5 shows the pen device (1) where in present needle and a cap (5) that would be associated with a pen. Needle cap (5) has an internal thread (6) that mates with the cartridge or syringe (2) and needle (9) extends on both sides of the needle cap (5). On attachment of needle cap (5) to the cartridge or syringe (2) by screw mechanism, needle (9) which extend on to the internal of the cap pierces the rubber seal (3) of the cartridge or syringe (2) and establishes contact with the biological material in the cartridge or syringe (2). Needle cap (5) may be removed and set dosage of the biological material may be administered to a patient.

FIG. 6 shows the proposed system wherein instead of needle (9) which protrudes out of the cap is replaced by a shortened needle which acts as a micro-needle.

While the present invention has been described in terms of its specific embodiments, certain modifications and equivalents will be apparent to those skilled in the art and are intended to be included within the scope of the present invention.

The invention claimed is:

1. A device for delivery of a biodegradable micro-needle across a biological barrier, wherein the micro-needle comprises a therapeutically active ingredient and a biodegradable polymer, the device comprises a micro-needle strip comprising one or more biodegradable micro-needles, a housing (7), a roll(1), a main piston (2), an auxiliary piston (4) and a cutter (8), and a mechanism to select the number of biodegradable micro-needles to be delivered; the device is characterized in that it comprises a mechanism to cut, position and discharge on to the skin, a selected portion of biodegradable micro-needle corresponding to a selected dose of the therapeutic active ingredient to be delivered; said mechanism comprises the cutter (8) and auxiliary piston (4) directly attached to the main piston (2).

2. The device as claimed in claim 1, wherein the geometrical shape of the biodegradable micro-needles is selected from the group consisting of cylindrical, conical, tapered, pyramidal, frustoconical and frustopyramidal.

3. The device as claimed in claim 1, wherein the cutting mechanism is a cutter, a razor, or a claw mechanism made of a sharp edged metal.

4. The device as claimed in claim 1, wherein main piston (2), auxiliary piston (4), and the roll (1) are made of metal, plastic, polymeric material and or combination thereof.

5. The device as claimed in claim 1, wherein biodegradable micro-needle has an outer diameter of from about 10 microns to 100 microns and a length of at least 100 microns.

6. The device as claimed in claim 1 wherein the therapeutically active ingredient is selected from the group consisting of one or more of peptides, proteins, carbohydrates, nucleic acid molecules, lipids and other pharmaceutically active ingredients or combinations thereof.

7. The device of claim 1, wherein the auxiliary piston (4) is attached to the main piston (2) circumferentially at an angle.

8. The device of claim 7, wherein the auxiliary piston (4) is attached to the main piston (2) at its end.

9. The device of claim 7, wherein the angle is from 30° to 180°.

10. The device of claim 1, wherein the cutter (8) is integrally attached to the main piston (2) circumferentially.

11. The device of claim 1, wherein the main piston (2) is of circular, rectangular or square shape.

12. The device of claim 1, wherein the auxiliary piston (4) is of circular, rectangular or square shape.

* * * * *